United States Patent [19]

Gelly et al.

[11] Patent Number: 5,027,822

[45] Date of Patent: Jul. 2, 1991

[54] ECHOGRAPHY PROBE WITH IMPROVED CONNECTION CIRCUIT

[75] Inventors: Jean-Francois Gelly, Valbonne; Jacques Elziere, Contes; Patrick Dubut, Tourrettes S/Loup, all of France

[73] Assignee: General Electric CGR SA, Issy les Moulineaux, France

[21] Appl. No.: 368,336

[22] PCT Filed: Nov. 24, 1987

[86] PCT No.: PCT/FR87/00462

§ 371 Date: Jul. 17, 1989

§ 102(e) Date: Jul. 17, 1989

[87] PCT Pub. No.: WO88/04090

PCT Pub. Date: Jun. 2, 1988

[30] Foreign Application Priority Data

Nov. 28, 1986 [FR] France .............................. 86 16660

[51] Int. Cl.[5] .............................................. A61B 8/00

[52] U.S. Cl. ............................. 128/661.01; 29/25.35; 310/336; 310/368

[58] Field of Search ...................... 128/660.09, 660.10; 73/625-626; 29/25.35; 310/336, 368

[56] References Cited

U.S. PATENT DOCUMENTS

| | | | |
|---|---|---|---|
| 4,217,684 | 8/1980 | Brisken et al. | 29/25.35 |
| 4,747,192 | 5/1988 | Rokurota | 29/25.35 |
| 4,894,895 | 1/1990 | Rokurohta | 29/25.35 |

FOREIGN PATENT DOCUMENTS

| | | |
|---|---|---|
| 0140363 | 5/1985 | European Pat. Off. . |
| 0145429 | 6/1985 | European Pat. Off. . |
| 2079102 | 1/1982 | United Kingdom . |

OTHER PUBLICATIONS

Patent Abstracts of Japan, vol. 8, No. 206(E-267) (1643), Sep. 20, 1984, & JP, A. 5990498 (Toshiba K.K.) May 24, 1984.

Patent Abstracts of Japan, vol. 5, No. 129(E-70) (801), Aug. 19, 1981, & JP, A. 5666992(Yokogawa Denki Seisakusho K.K.) Jun. 5, 1981.

*Primary Examiner*—Francis Jaworski

*Attorney, Agent, or Firm*—Oblon, Spivak, McClelland, Maier & Neustadt

[57] ABSTRACT

When making curved bar probes it is necessary, particularly at high frequency, to provide circuits for the connection of piezoelectric elements of the bars which are compatible with the curvature imposed to the bar after it has been fabricated flat. The invention overcomes such difficulty by adjoining on both sides of the elements a generally parallelepipedic relay metallized on at least two (12,13) of its adjacent faces to transpose one connection face (7) situated in plane which must be curved into one connection face (13) which is perpendicular and of which the orientation remains unchanged and parallel to a same plane during the curvature operation. As a result, the connection is simplified.

12 Claims, 3 Drawing Sheets

ECHOGRAPHY PROBE WITH IMPROVED CONNECTION CIRCUIT

BACKGROUND OF THE INVENTION

An object of the present invention is a echograph probe with improved connection circuit It finds application more particularly in the medical field where probes of this type are used for echographic examinations capable of enabling the internal structures of the tissues of an examined human body to be revealed It can, nonetheless, find application in all the other fields of industry where use is made of echographs, the acoustic signal frequency of which is high. For, the raising of this frequency causes a corresponding reduction in the size of the probes. The result thereof is specific problems of connection due to miniaturization. The present invention proposes a solution thereto.

DISCUSSION OF BACKGROUND

An echograph comprises, in principle, means to transmit an electrical signal vibrating at an acoustic frequency, a transducer probe receiving this electrical signal and converting it into a mechanical excitation, this probe being applied against a medium to be subjected to an acoustic signal. The back-reflected signal that results from the subjecting of the medium to an acoustic signal is generally received by the same probe during stops in transmission. The probe, which is thus reversible, reconverts the acoustic signal that reaches it into an electrical signal This is applied to receiving elements In the probe, the means that perform the conversion of an electrical signal into an acoustic signal and/or vice versa comprise, in a known way, elements of a piezoelectric crystal. The connection device which is an object of the invention concerns the electrical connection of the all the elements of the probe. In one probe, the piezoelectric elements are generally aligned with one another to form a bar. With respect to the acoustic phenomenon, there is distinguished, on this bar, a front face, on the side where the useful acoustic signal is propagated, and a rear face opposite to the front face.

The process of electrical/acoustic conversion takes place most efficiently when the front and rear faces of the elements of the bar are provided with electrodes. During transmission, the electrical signal is applied to these electrodes, it causes the existence of an alternating electrical field in the piezoelectric crystal. This crystal vibrates and emits an acoustic signal. The reverse occurs at reception. The dimensions of the piezoelectrical elements are preferably calculated as a function of the working acoustic frequency of the probe and as a function of the speed of propagation of the waves in the crystal. These two dimensions determine the wavelength $\gamma$ of the acoustic vibration in the crystal. In the bar, the piezoelectric elements are aligned side by side, parallel to their length, and their height is the distance between the two electrodes. Under these conditions, it is known that the length of the elements should be greater than ten times $\gamma$, that the height should be substantially equal to $\gamma/2$, and that the width, measured orthogonally with respect to these first two dimensions should be smaller than or equal to $\gamma/6$. In taking into account a propagation speed of the order of 1500 meters per second, and a working frequency of the order of 7.5 MHz, the elements of the bar should have a width and, hence, a connection pitch smaller than or equal to about 30 micrometers. Furthermore, to prevent stray phenomena of diaphony between adjacent piezoelectrical elements, the method of cutting the piezoelectric elements at their midwidth is known. This has the effect of dividing the connection pitch by two. It becomes of the order of 15 micrometers.

To make the connections, solutions have been developed, in the prior art, inspired by semiconductor technology. In these solutions, a layer of connection wires is applied against each face of the bar. In both these layers, individual connections are assigned to each of the electrodes separated by piezoelectric elements. During fabrication, the two layers extend on either side of the bar like two wings. To reduce the space factor of a probe of this type, these two wings are subsequently folded backwards. But, the development of the art has now established the use of curved bar probes. In these bars, the alignment of the elements has a convex, curved shape adapted, on the one hand, to a direct contact with the bodies to be examined and having an effect, on the other hand, the effect of limiting the number and complexity of the electronic control circuits of these bars during their use in sector scanning. For obvious reasons of simplicity, the bars are first of all fabricated flat on a flexible support then subsequently curved. It was then observed that the connection technique recommended was unusable. It is not possible to curve the layers twice in orthogonal directions.

In a European patent application No. 84 304 373.4, filed on 3rd Dec. 1984, a solution was proposed to the connection problem resulting from the curvature of the bars. In this solution, groups of adjacent elements are connected to layers of small dimensions (since the number of elements in a group is smaller than the number of elements of the bar). When the bar is curved, these layers are designed to occupy, in space, layers superimposed on one another. This technique does not, however, give entire satisfaction. It was noticed that the stresses exerted during the curvature by a layer, even small-sized, on the elements of the group to which it is connected, had the effect of breaking the continuity of the general curvature of the bar; it being possible, at a stretch, to consider this curvature as a sequence of segments in broken line approaching the theoretical curve to be achieved. The result thereof is a distortion of the pictures produced by the echograph, which hampers the interpretation of their meaning. The solution to this problem which would consist in making layers with a single connection per layer, assigned in this case to a single element, is unusable in view of the number of elements that a bar must comprise: the largest number possible (typically 128). Since the number of connections to be made could be equal to thrice the number of elements, it would then be necessary to manipulate a big hank of wires which, moreover, are made fragile by their small size (of the order of 5 micrometers in diameter).

Another connection solutions, for example as described in EP-A-140 363 or in GB-A-2 079 109 are foreseeable. Meanwhile they do permit neither the later forming of the probe nor, at a same time, the independency of the electrical connections.

SUMMARY OF THE INVENTION

An object of the invention is a truly industrial-scale solution to this problem of fabrication. In the invention, use is made, beside each element, of a relay which takes the form of a parallelepiped block displaying the particular feature of being metallized on at least two adjacent faces. This relay therefore includes the desired fold in itself. In effect, by one of its faces, it can be connected, in one and the same plane, with an electrode of the element. By its other face, electrically connected to the first one, it can be connected to a connection circuit which is presented orthogonally. This solution, which is particularly useful in the context of the use of concave as well as convex, curved bars, can, of course, be used also with straight bars, bars in broken lines, etc.: it replaces the folding of the layers.

The invention concerns an echograph probe of the type comprising aligned piezoelectrical elements, mounted on a support common to all the elements, and electrical connection means to connect electronic circuits to these elements, characterized in that the connection elements comprise, adjacent to at least one side of the alignment and at right angles to each of the elements, at least one relay block in a generally parallelepiped shape, metallized on at least two of its adjacent faces, and fixed to the support.

BRIEF DESCRIPTION OF THE DRAWINGS

The invention will be better understood from the reading of the following description and from an examination of the figures that accompany it. These are given solely by way of indication and in no way restrict the scope of the invention. In the figures, the same references designate the same elements. The figures show.

DETAILED DESCRIPTION OF THE PREFERRED EMBODIMENT

Figure 1:
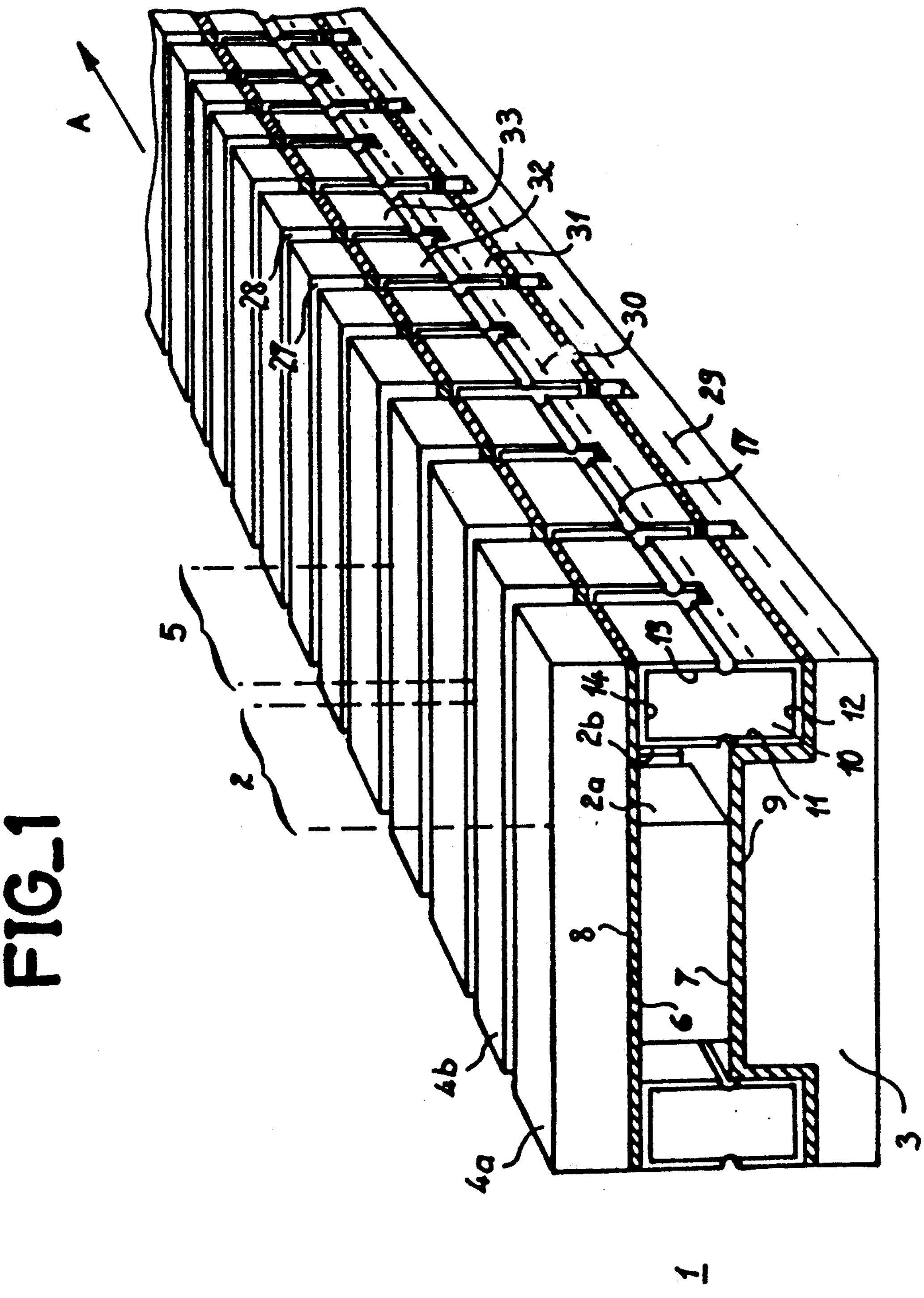
FIG. 1: a part of an echograph probe according to the invention.

Figure shows a bar of an echograph probe according to the invention. The bar I comprises piezoelectric elements: for example the element 2 formed by two half-elements 2*a* and 2*b*. These elements are aligned, and mounted between a support 3, common to all the elements, and acoustic transition blades such as 4, divided into two half-blades 4*a* and 4*b*, assigned to each of these elements. An element 2 is thus composed of two half elements, this division being used to resolve problems of diaphony that may appear between two adjacent elements, for example the elements 2 and 5. The front 6 and the rear 7 faces of each element are respectively provided with a metallization 8, 9, used to induce an electrical field in the element when an electrical signal is applied to them. The metallizations of the front and rear faces enable an electrical field to be applied parallel to the direction of propagation of the acoustic waves. This arrangement is advantageous because it improves the coupling coefficient- between the electrical field and the acoustic field.

The piezoelectric elements comprise, for example, elements made of plastic such as, for example, $PVF_2$ or copolymer $PVT_2F$; a ceramic such as, for example, PZT, polymer compound PZT or $PBTiO_3$ or a crystal.

What characterizes the invention is essentially the presence, on at least one side of the alignment A of elements, herein, for example, to the right, of generally parallelepiped shaped blocks assigned to each of the elements (the block 10 is assigned to the element 2), and having the particular feature of being metallized on at least two of their adjacent faces. Here, the faces 11 to 14 of the block 10 are even all metallized. The result thereof is that the metallizations 8 and 9 of the elements, made in planes parallel to the plane of the bar, can be connected simply, in parallel planes, to metallized faces of the block. And the continuity of the metallization, vertical to the adjacent faces of the blocks, gives a possibility of electrical connection to these elements in planes which are now perpendicular to the plane of the bar. Thus, the operation equivalent to the folding of the layers has been achieved. The relay blocks may have any shape. With the characteristic feature of a parallelepiped shape, it is understood that these blocks have at least two metallized faces located in two substantially perpendicular planes.

Figure 2A:
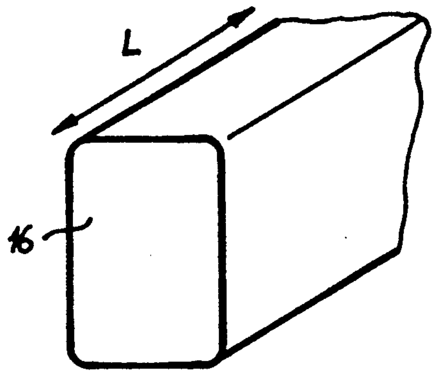
FIGS. 2*a*, 2*b*, 2*c*, 2*d*, and 2*e*: steps of method of assembly of the connection circuits of the invention.
Figure 2B:
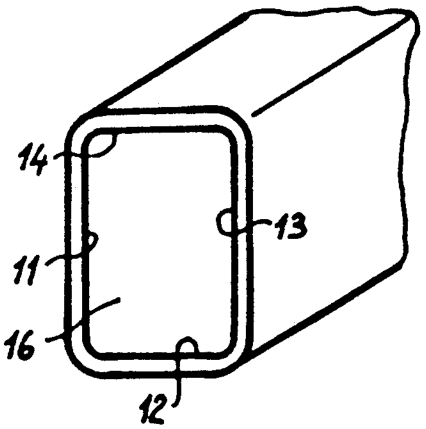
Figure 2C:
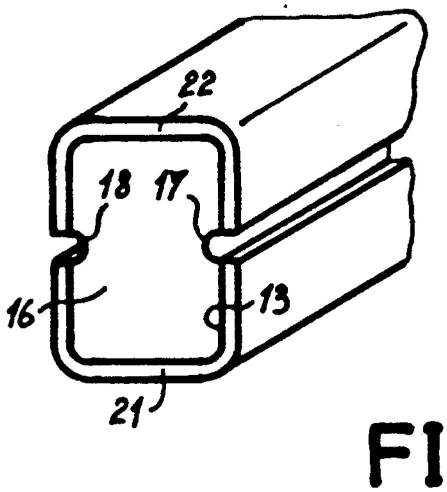

In examining FIGS. 2*a* to 2*c*, we shall examine a general method for the fabrication of a bar according to the invention. On a thin support 3, made of polyurethane for example, with a general shape of an upside-down T, a metallization is made by a known process. For example, by vacuum evaporation/spraying or again by electrolysis. Then, on top of the central part of this support, there is fixed a bar of a piezoelectric crystal 15 in which the elements will be subsequently be cut. Furthermore, ceramic strips (FIG. 2*a*) are made, the length L of which is equal to the length of the crystal 15, that is, the length needed to make the bar. The strip 16 is then metallized on all its faces 11–14 so as to provide for electrical continuity at its periphery. Then, by a simple grooving operation (FIG. 2*c*), the metallization is separated into two metallizations 21 and 22 which are electrically independent. For example, grooves 17, 18 are made through the metallization up to the ceramic body of the strip. In a preferred embodiment two strips are made in the same way for each bar. Each strip 16 and 19 is then fixed on either side of the crystal 15 on top of the arms 23 and 24 of the support 3. The general upside-down T shape of the support is turned to advantage to secure the strips 16 and 19 on either side of this support.

Figure 2D:
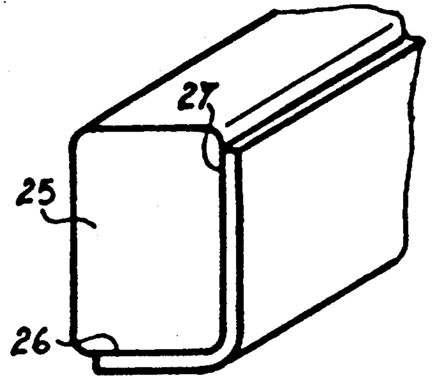
Figure 2E:
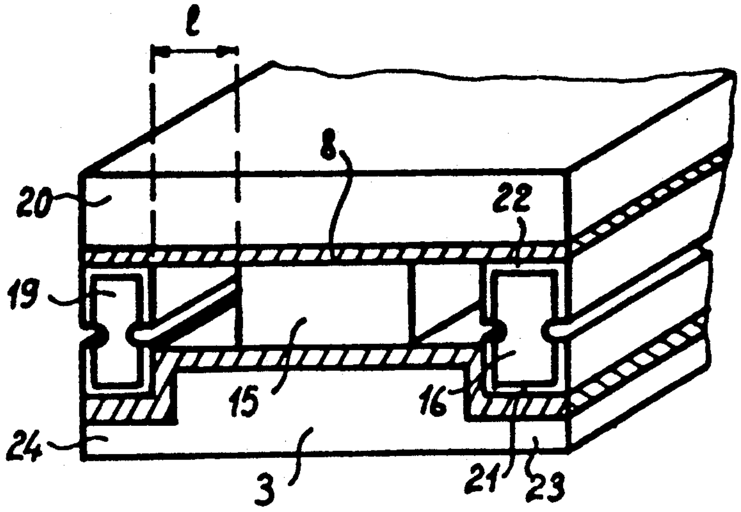

By similar techniques, a so-called transition blade 20 is then made, the thickness of which, in a known way, is equal to a quarter of the future working acoustic wavelength of the probe. This blade is metallized on its lower face. The blade is then fixed to the crystal 15 and to the strips 16 and 19. One of the two metallizations of each strip, the metallization 21 may then come into contact with the metallization of the support 3, on a vertical flank and on a horizontal flank of this support; while the other metallization, the metallization 22, may make contact beneath the metallization of the blade 20. Since the two metallizations 21 and 22 come on to the lateral face 13 of the strip 16, we have thus succeeded in presenting electrically, on a lateral face perpendicular to the plane of the crystal 15, the metallizations of the upper and lower faces of this crystal. The electrical continuity between the metallization 8 of one face of the crystal, the metallization of the blade 20 and the metallizations 22, on the one hand, and between the metallization 9, the metallization of the support and the metallizations 21, on the other hand, is ensured by pressing and bonding with bonders which may possibly be conductive. In view of the precision of implementation needed to fabricate the crystal, the strips, the blade and the support, a perfect assembly is obtained by bringing, if necessary, the flexibility of the blade 20 into play. To this end, an elastic space e may even be made between the boundary of the edge of the crystal and the boundary of the strips so as to enable the flexion of this blade.

a variant, the strips can be metallized as indicated in FIG. 2*d*. In this figure, the strip 16 has only one metallization extending from a face 26 to a face 27. It is possible, in this way, to replace the strips 16 and 19 by two strips 25 which, however, are rotated by a half turn, from one side to the other of the crystal 15. For example, on the right-hand part of the crystal, the metallization of the face 16 will be in contact with the metallization of the arm 23 of the support 3, and the lateral, vertical metallization 27 would be assigned to its connection by the right of the bar. On the left-hand side of the bar, the metallization 26 will be in contact with the metallization of the blade 20 while the lateral, vertical metallization 27, presented to the left this time, would ensure the continuity thereof. In this way, it is possible to accede electrically to the other electrode of the crystal 15 by the left. Once these assembling operations are performed, the bar of piezoelectric elements is cut in the composite rod thus formed. In a known way, cuts are made, for example, with a saw, along this rod, with a chosen pitch. In a preferred way, cuts 27 (figure between elements are deeper than cuts 28 inside one and the same element. The reminder, indicated by dashes 29, of the base of the cuts 27, shows that these cuts extend up to the support 3, namely beneath the base of the strips. Consequently, the strips are cut up into series of blocks (such as 10) each assigned ipso facto to a piezoelectric element. The intermediate cuts 28 are made in the middle of each element up to a depth indicated, as a reminder, by dots and dashes 30, the plane of which underlies the altitude of the groove 17 which, in the preferred version, separates the metallizations of the strips 16 into two electrically independent metallizations. The result thereof is to make it possible, for one and the same element, to reach its lower electrode by a connection applied to a side face 31 of the relay block of this element. The upper electrodes of each of the two half elements forming this element are reached by the metallizations 32 and 33, which belong to one and the same block and have been electrically separated from each another by the cut 28. It is observed that the connections 31 to 33 are effectively located in a plane which is now perpendicular to the plane of the bar 1.

Figure 3A:
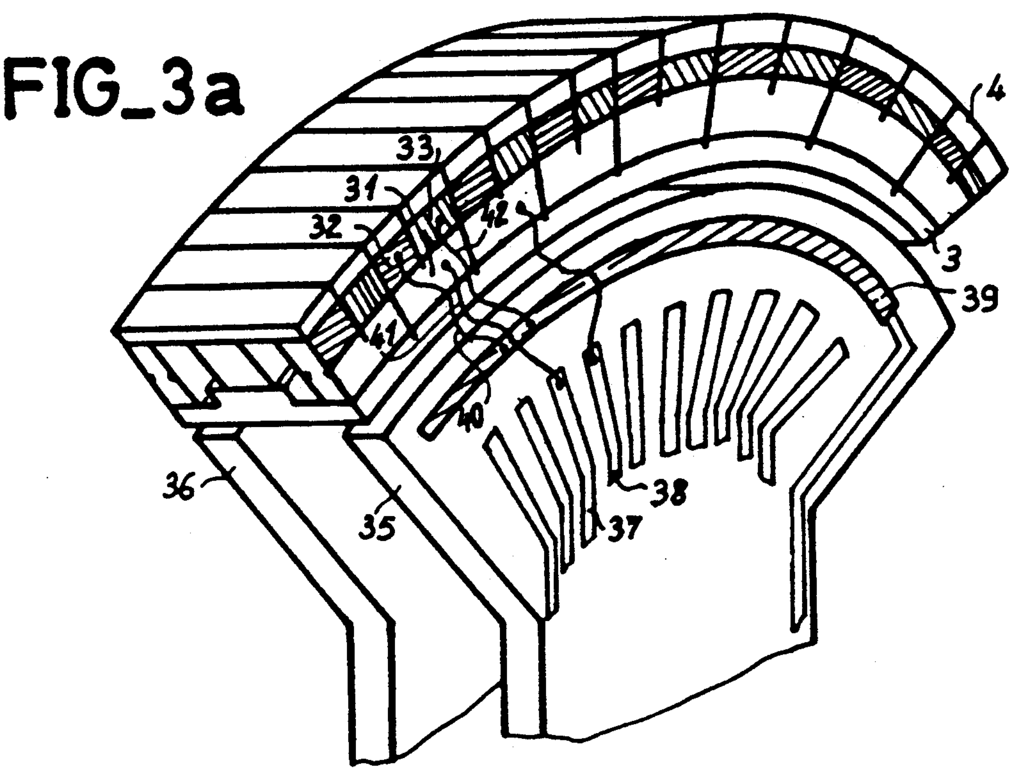
FIGS. 3*a* and 3*b*: two variants of electrical connections of the elements of a probe provided with the improvement of the invention.
Figure 3B:
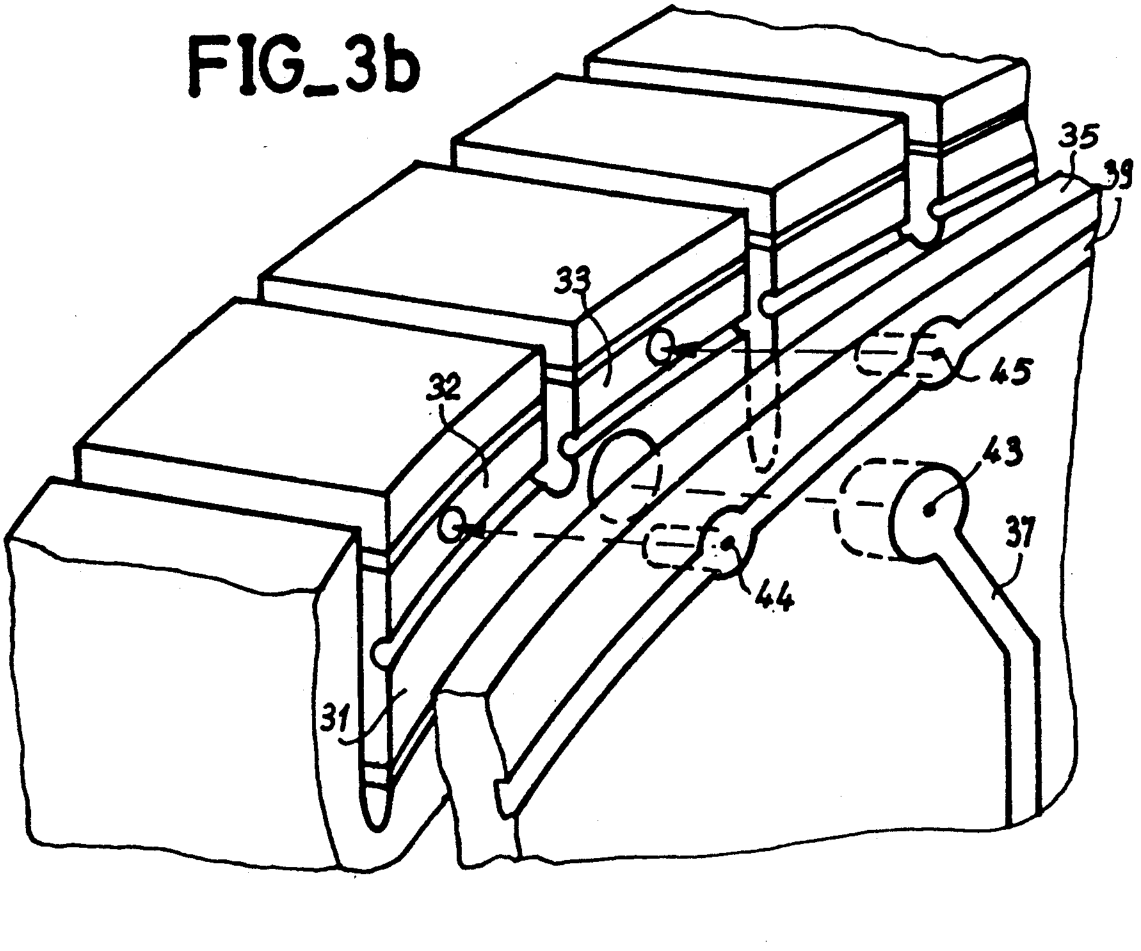

FIGS. 3*a* and 3*b* show exemplary embodiments of the rest of the connection means, the making of which is simplified because of the invention. On the one hand, as was declared, the invention is more particularly valuable in the case of the making of curved bars. The curvature is obtained after making the separations 27 and 28 in applying the deformable support 3 on an adequate curved form. The micro-assembly-solution shown in FIG. 3*a* comprises; with the preferred variant with grooving 7, 18 of totally metallized strips, two printed circuits 35, 36 (obtained, for example, by etching) each having a flared-out part, the head of which is rounded so as to get imbricated beneath or near the curved support 3. Each printed circuit has a number of tracks 37, 38 which get flared out like a corolla in the head of the circuit. The number of tracks is equal to the number of piezoelectric elements of the probe. In addition to the tracks 37, 38, these printed circuits have a track 39 which crowns the circuit. The track 39 is designed to be connected, by electrical connection wires 40 and 42, to the connections 33 and 32 of each of the parallelepiped blocks. The ends of each of the tracks 37 and 38 are designed to be connected by connecting wires 41 to the connections 32 of the parallelepiped blocks. Similar connections are made for the circuit 36.

These connections provide, with respect to the prior art assembly referred to, an additional advantage of symmetry of connection. In effect, in the prior art referred to, a connection relative to one of the faces of the elements was organized on only one side of the bar, while the other connection (on the other side of the elements) was organized on the other side of the bar. The result thereof a harmful modification of working of the piezoelectric crystal. In the invention, the supply by one and the same side of the bar or, better still, in a preferred way, by both sides of the bar at the same time, of the two electrodes of each element, has the effect of preventing this drawback. The technique used to make the connections 40 to 42 is derived from a connection technique of the type used in semiconductor technology. It is perfectly capable of being applied industrially because of the regular pitch values in the distribution of the connections 40 and 42, on the one hand, and the connections 41 on the other. This operation, which is very precise, can therefore be automated provided, in front of the machine that performs it, the bar/printed circuits assembly is subjected to a circular movement.

In one variant shown in FIG. 3*b*, the connection technique used is a so-called remelting technique. In this technique, a printed circuit such as the circuit 35 is brought near each side of the curved bar. The circuit 35 has, vertical to the ends of the tracks and facing the crowning track, metallized holes 43 and 45. These metallized holes are placed in front of the faces 31 to 33 respectively of the relay blocks of each of the piezoelectric elements. The metallization of these holes as well as the metallization of these lateral faces is adapted to receive a tiny drop of indium obtained by growth. Before the remelting operation, the printed circuit is applied against the bar so that the corresponding drops touch each other. Then, by moderate heating (90°) under vacuum, the remelt heat operation is done. In these conditions, the drops get melted in one another as well as in the metallizations which carry them. The advantage of this solution is that all the blocks and, hence, all the elements, are connected simultaneously. Other operations are then performed in a standard way. In particular, a connector is made to connect the probe to its electronic circuits (not shown) as well as a sheath for the protection of the probe thus made.

We claim:

1. An echograph probe comprising: piezoelectrical elements, mounted in a side-by-side alignment on a support common to all the elements, and electrical connection means to connect electronic circuits to said elements, said electrical connection means comprising, adjacent to one side of said side-by-side alignment and facing each of said elements, at least one insulating relay block in a substantially parallelepiped shape, metallized on at least two of its adjacent faces, and fixed to the support.

2. Probe according to claim 1, wherein the said elements are each covered with an acoustic transition blade and said at least one block is inserted between said support and said blades.

3. Probe according to claim 2, wherein said alignment is curved.

4. Probe according to claim 3, wherein said alignment is convex.

5. Probe according to claim 3, wherein said alignment is concave.

6. Probe according to any one of the claims 2 to 5, wherein said electrical connection means comprise, facing each element, two blocks inserted respectively on either side of this element, between said support and a transition blade.

7. Probe according to any one of the claims 2 to 5, wherein said at least one is metallized by metallization on at least three contiguous faces, and said metallizations form two electrically independent contact surfaces designed to connect the faces of the elements applied respectively against the support and against the blade.

8. Probe according to any one of the claims 2 to 5, wherein said electrical connection means comprise a printed circuit and a set of connection wires connecting metallizations of said at least one block to printed connections on said printed circuit.

9. Probe according to any one of the claims 2 to 5, wherein said electrical connection means comprise a printed circuit and drops of a metal to be remelted deposited on the lateral faces of said at least one block and on connections made on said printed circuit.

10. Probe according to any one of the claims 2 to 5, wherein the at least one block include at least one intermediate groove to separate metallizations.

11. Probe according to any one of the claims 2 to 5, wherein at least one block include an intermediate separation for one block to be capable of being connected to adjacent half piezoelectrical elements.

12. Probe according to any one of the claims 2 to 5, further comprising a space of elasticity (e) between lateral edges of elements and of said at least one block corresponding to said elements.

* * * * *